United States Patent [19]

Yoshioka et al.

[11] Patent Number: 4,810,301

[45] Date of Patent: Mar. 7, 1989

[54] COMPOSITION FOR SIZING AGENT AND PROCESS FOR USING THE SAME COMPOSITION

[75] Inventors: Shigehiko Yoshioka, Akashi; Tsuneo Yoshida, Nagaoka; Hisatake Sato, Yokohama; Hideto Yamada, Akashi; Yoshio Adachi, Nishinomiya, all of Japan

[73] Assignees: Seiko Kagaku Kogyo Co., Ltd.; Nippon Oil Co., Ltd.; Hokuetsu Paper Mills, Ltd., all of Japan

[21] Appl. No.: 104,970

[22] Filed: Oct. 6, 1987

Related U.S. Application Data

[62] Division of Ser. No. 780,083, Sep. 25, 1985, Pat. No. 4,717,452.

[51] Int. Cl.$^4$ ................... C09K 3/00; D21H 3/08
[52] U.S. Cl. ................... 106/287.24; 162/158
[58] Field of Search ................ 106/287.24, 287.29

[56] References Cited

U.S. PATENT DOCUMENTS

| | | | |
|---|---|---|---|
| 3,102,064 | 8/1963 | Wurzburg | 162/158 |
| 4,545,855 | 10/1985 | Sweeney | 162/158 |
| 4,576,680 | 3/1986 | Kawatani | 162/158 |
| 4,606,773 | 8/1986 | Nuvak | 106/213 |
| 4,717,452 | 1/1988 | Yoshioka et al. | 162/158 |

FOREIGN PATENT DOCUMENTS

| | | |
|---|---|---|
| 1186857 | 5/1985 | Canada. |
| 41056 | 12/1981 | European Pat. Off. |
| 2006744 | 5/1979 | United Kingdom. |
| 1601464 | 10/1981 | United Kingdom. |

OTHER PUBLICATIONS

WO 85/00627 Yoshioka et al. Feb. 1985.
Schonfeldt "Surface Active Ethylene Oxide Adducts", pp. 655–657, Sep. 1971.
Abstract Bulletin of the Institute of the Paper Chemistry, vol. 57, No. 1, Jul. 1986, p. 134, Abstract No. 1087.
Chemical Abstract vol. 103, No. 4, Jul. 1985, p. 79, Abstract No. 24007d.
Abstract Bulletin of the Institute of Paper Chemistry, vol. 54, No. 11, May 1984 p. 1340, Abstract No. 12666.
Abstract Bulletin of the Institute of Paper Chemistry, vol. 54, No. 3, Sep. 1983, p. 350, Abstract No. 3226.
Abstract Bulletin of the Institute of Paper Chemistry, vol. 55, No. 2, Aug. 1984, pp. 245–246, Abstract No. 2297.
Kaimen–Kasseizai Binran, pp. 20–21, Jul. 5, 1960.
Organic Chemistry, 3d Ed., Fieser et al., pp. 188–189, 1956.
Casey, "Chemistry and Chemical Technology", *Pulp and Paper*, 3d Ed., vol. III (1981) pp. 1491–1494.

*Primary Examiner*—Theodore Morris
*Attorney, Agent, or Firm*—Parkhurst, Oliff & Berridge

[57] ABSTRACT

A composition for a sizing agent comprising (a) 70–99.9 wt.% of a substituted alkyl succinic anhydride or a substituted alkenyl succinic anhydride or a mixture of these succinic anhydrides, and (b) 0.1–30 wt.% of phosphates of polyoxyethylene alkyl ether esters or phosphates of polyoxyethylene alkyl aryl ether esters of a mixture of these phosphate esters and a process for using the composition by dispersing the composition, adding the produced aqueous dispersion to pulse alurry of paper making material, and making the paper. This composition for the sizing agent has excellent storage stability and underwater self-emulsion, and accordingly exhibits an excellent sizing effect and provides paper having an excellent sizing effect.

3 Claims, No Drawings

COMPOSITION FOR SIZING AGENT AND PROCESS FOR USING THE SAME COMPOSITION

This is a division of application Ser. No. 780,083 filed Sept. 25, 1985 now U.S. Pat. No. 4,717,452.

BACKGROUND OF THE INVENTION

The present invention relates to a composition for a sizing agent comprising a mixture of a substituted alkyl succinic anhydride or a substituted alkenyl succinic anhydride and or a mixture of these succinic anhydrides, phosphates of polyoxyethylene alkyl esters or phosphates of polyoxyethylene alkyl aryl ethers or a mixture of these phosphates of esters; and to a process for using the composition for the sizing agent by dispersing the composition in aqueous solution of aqueous soluble polymer compound, adding the obtained aqueous dispersant in a pulp slurry of paper making raw material, and then making paper and, more particularly, to a composition for sizing paper having excellent storage effect and preferable underwater self emulsion, and a process for making paper having excellent sizing effect by using the composition.

There is known a sizing agent and particularly a paper making sizing agent such as a mixture homogenized by mechanically agitating an aqueous solution of cationic starch and a substituted succinic anhydride in an aqueous dispersion to be mixed with a pulp slurry, a dispersion of mixture of premixing a substituted succinic anhydride and nonionic surfactant of certain type in water (in Japanese Patent Publication No. 36044/1978), or an aqueous dispersion of a substituted succinic anhydride and underwater oil type surfactant dispersed in a substituted succinic anhydride having diameters of ultrafine particles dispersed in an aqueous solution of ampholitic acrylamide polymer (in Japanese Patent Laid-open No. 45,731/1983). A large scale apparatus is required in the case of producing the dispersion by using cationic starch of these aqueous dispersions, and yet it is difficult to sufficiently finely pulverize the dispersion particles in the obtained aqueous dispersion. Therefore, the sizing agent has a drawback that the sizing effect of the dispersion is deteriorated, and the aqueous dispersions of the latter two having inadequate storage stability of the composition before the aqueous dispersion of the latter two is dispersed in the aqueous dispersion, and as time is elapsed, the under water dispersant is erased, and the sizing performance is largely decreased. Consequently, the mixture composition must be adjusted immediately when used as the sizing agent, and there is a problem in a practical use in an industrial scale.

In order to solve the above-described problems, the present inventors have proposed an aqueous dispersion containing a surfactant having a substituted succinic anhydride and a half ester residue of the substituted succinic acid (in Japanese Patent Application No. 154984/1982), but in the aqueous dispersion, when a substituted alkenyl succinic anhydride of an additive reaction product of a straight chain internal olefin and maleic anhydride is used as the substituted succinic anhydride, sufficient underwater dispersing effect cannot be obtained unless the above-described surfactant is mixed in large quantity, and the large quantity of surfactant substance disturbs the sizing effect. Therefore, it is found that excellent sizing effect cannot be obtained.

SUMMARY OF THE INVENTION

Accordingly, an object of the present invention is to provide a composition for a sizing agent which exhibits excellent storage stability and underwater self-emulsion and hence excellent sizing effect comprising (a) 70-99.9 wt. % of a substituted alkyl succinic anhydride or a substituted alkenyl succinic anhydride and or a mixture of these succinic anhydrides, (b) 0.1-30 wt. % of phosphates of polyoxyethylene alkyl ether esters or phosphates of polyoxyethylene alkyl aryl ether esters or a mixture of these phosphate esters, and a process for effectively making paper having excellent sizing effect by using the composition for the sizing agent, i.e., a process for using the composition for a sizing agent.

DESCRIPTION OF THE PREFERRED EMBODIMENTS

A composition for a sizing agent of the present invention consists of (a) 70-99.9 wt. % of a substituted alkyl succinic anhydride or a substituted alkenyl succinic anhydride or a mixture of these succinic anhydrides, and (b) 0.1-30 wt. % of phosphates of polyoxyethylene alkyl ether esters or phosphates of polyoxyethylene alkyl aryl ether esters or a mixture of these phosphate esters.

A substituted alkyl succinic anhydride or a substituted alkenyl succinic anhydride in the composition for a sizing agent may employ any of the compounds heretofore known per se as a sizing agent, and concretely employ a substituted succinic anhydride having 8 or more carbons and preferably 12-36 carbon alkyl group or alkenyl group. This substituted succinic anhydride can be readily produced generally by utilizing alpha-olefin, inner olefin or the additive reaction of an alpha-olefin, inner olefin or their mixture having carbon atoms of corresponding number or their mixture, and utilizing the additive reaction of these mixtures with maleic anhydride. Particularly, when the substituted succinic anhydride is, for example, octadecene-9, tetradecene-7, hexadecene-7, eicosane-11 or their mixtures, straight chain inner olefin mixture in which double bond produced by dehydrated reaction of a straight chain paraffin is substantially uniformly distributed at the positions except alpha-position, additive reaction product of inner olefin and maleic anhydride of straight chain inner olefin mixture having 70% or more of total amount of inner olefin disposed at 2-, 3- and 4-position of double bond produced by anisotropic reaction in the presence of a catalyst with straight alpha-olefin, i.e., substituted alkenyl succinic anhydride having succinic anhydride group in a substituted group, the sizing effect effected by the composition for the sizing agent of the present invention is improved.

Other phosphates of polyoxyethylene alkyl ether esters or phosphates of polyoxyethylene alkyl aryl ether ester are preferably compounds represented by the following general formula:

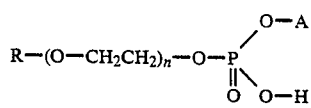

where R is an alkyl or alkyl aryl group having 8 or more carbon atoms; A represents H or $R'-(O-CH_2CH_2)_m$; n is an integer greater than or equal to 1; (R' is an alkyl or alkyl aryl group; m is an integer greater than or equal to 1. Particularly, when the R of the above general formula is alkyl or alkyl aryl group having 10-20 carbon atoms and the value of n is 5 or more, the underwater dispersion particles of the produced substituted succinic anhydride becomes extremely fine, and the sizing effect exhibited by the composition of the present invention becomes very excellent.

In the mixture of (b) the phosphates of esters in the same manner as (a) the substituted succinic anhydride, the mixture of (a) 70-90 wt. % of substituted succinic anhydride and (b) 10-30 wt. % of the phosphates of esters produces a water dispersion containing substituted succinic anhydride of sufficiently fine particle size by merely mixing the mixture, thereby providing a so-called self-emulsion type paper making sizing agent. Further, the mixture of (a) 90-99.9 wt. % of substituted succinic anhydride and (b) 0.1-10 wt. % of the phosphates of esters disperses in aqueous solution of aqueous polymer compound in the mixture, thereby producing aqueous dispersion of substituted succinic anhydride of fine particle size sufficiently stable by mixing means of the degree for extremely slowing agitating. Therefore, when the mixture of (a) the substituted succinic anhydride and (b) the phosphates of esters is used as the paper making sizing agent, it is preferable to use aqueous dispersion utilizing aqueous solution of aqueous soluble polymer compound due to the relationship of reducing the mixture amount of (b) the phosphates of esters so as to reduce the sizing effect disturbing action caused by (b) the phosphates of esters as small as possible.

According to the present invention a process for making paper of a process for using a composition for a sizing agent comprises adding an aqueous dispersion that comprises a mixture of (a) 70-99.9 wt. % of substituted alkyl succinic anhydride or substituted alkenyl succinic anhydride or their mixture of these succinic anhydrides and (b) 0.1-30 wt. % phosphates of polyoxyethylene alkyl ether esters or phosphates of polyoxyethylene alkyl aryl ether esters or their mixture of these phosphates of esters in aqueous solution of aqueous soluble polymer compound to pulp slurry of paper making material, and then making the paper in accordance with an ordinary method to provide paper.

In the aforementioned paper sizing process, the aqueous soluble polymer compound contained in the aqueous dispersion may employ not only cationic starch, ampholytic acrylic amide polymer heretofore known per se, but also other aqueous soluble starch derivatives, aqueous soluble cellulose derivatives, various acrylic amide polymers, polyvinylalcohol, polyethylene imine and its derivatives, aqueous soluble polyamide, aqueous soluble acrylic resin, aqueous soluble polyester, aqueous soluble maleic resin, and various aqueous soluble vinyl polymers. The aforementioned aqueous soluble polymer compounds contained in the aqueous soluble dispersion is preferably in a range of 0.1-5 wt. parts and preferably 0.5-2 wt. parts to 1 wt. parts of substituted succinic anhydride in the aqueous soluble dispersion.

In the process for making paper of process for using a composition for a sizing agent of the present invention, known chemicals may be used in the sizing step of adding aqueous dispersion of the sizing agent into a pulp slurry such as paper strength intensifier, filtrate accelerator, filler yield agent, fixing agent or other sizing agent.

As another process, the aqueous dispersion of the produced substituted succinic acid is coated on wet paper or semidried paper by suitable known means after making or sheet making, thereby enabling surface sizing.

The composition for a sizing agent of the present invention constructed as described above consists of a mixture of specific surfactant and substituted succinic anhydride. Since the surfactant has excellent solubility to the substituted succinic anhydride, excellent storage stability is provided irrespective of the type of the substituted succinic anhydride, stable underwater self-emulsion is provided, aqueous dispersion of substituted succinic anhydride having extremely fine particle size is provided in the presence of a small amount of surfactant, and excellent operation is provided as the composition for the paper making sizing agent of various types.

Since a process for making paper and a method for using the composition for the sizing agent of the present invention adds the aqueous dispersion of substituted succinic anhydride having the above-described characteristics as sizing agent in paper making pulp slurry, it can eliminate the complexity of preparing the composition immediately before using without a large scale emulsifying apparatus to produce aqueous dispersion. Therefore, it is effective to make paper having excellent sizing effect in an industrial scale.

Hereinafter, the present invention will be described further in detail by the preferred examples thereof as compared with reference examples of making paper utilizing the composition for the sizing agent and the aqueous dispersion of the composition of the present invention as the sizing agent, and the properties of the aqueous dispersion of the composition and the sizing effect of the paper will be moreover described.

EXAMPLE 1

Comparison Example 1

Substituted alkenyl succinic anhydride and surfactant listed in predetermined columns of Table 1 are utilized, both are agitated and mixed under slow heating condition at an ambient temperature of 40° C. or lower, and compositions (a), (b), (c), (d) for sizing agent of the present invention and compositions (1), (2) for comparison are prepared.

The substituted alkenyl succinic anhydride A is maleic anhydride reacted with inner olefin having 15-18 carbon atoms, and the substituted alkenyl succinic anhydride B is maleic anhydride reacted with oligomer mainly containing pentamer of propylene.

TABLE 1

| Composition | Substituted alkenyl succinic anhydride | Surfactant |
| --- | --- | --- |
| (a) | A<br>80 wt. % | Phosphates of polyoxyethylene nonyl phenol ether ester (mono-, di-mixture)<br>(polyoxyethylene: n = 9)<br>20 wt. % |
| (b) | B<br>85 wt. % | Phosphates of polyoxyethylene nonyl phenol ether ester (mono-, di-mixture)<br>(polyoxyethylene: n = 9)<br>15 wt. % |
| (c) | A<br>85 wt. % | Phosphates of polyoxyethylene nonyl phenol ether ester (mono-, di-mixture)<br>(polyoxyethylene: n = 21.5)<br>15 wt. % |
| (d) | B | Phosphates of polyoxy- |

TABLE 1-continued

| Composition | Substituted alkenyl succinic anhydride | Surfactant |
|---|---|---|
| | 90 wt. % | ethylene nonyl phenol ether ester (mono-, di-mixture) (polyoxyethylene: n = 21.5) 10 wt. % |
| (1) | A 80 wt. % | Polyoxyethylene nonyl phenol ether (polyoxyethylene: n = 15) 20 wt. % |
| (2) | B 85 wt. % | Sulfates of polyoxyethylene olenyl ether ester ammonium (polyoxyethylene: n = 18) 15 wt. % |

EXPERIMENT 1

1 wt. parts of compositions (a) to (d) and (1), (2) provided in the example and comparison example are mixed with 99 wt. parts of water, agitated, dispersed to prepare aqueous dispersions of different types.

The prepared aqueous dispersions are added to 2 wt. % pulp slurry containing 20 wt. % of pulp (L-BKP, c.s.F. 400 cc) of heavy calcium carbonate filler (Escalon #800 made by Sankyo Powder Co.) so that the composition in the aqueous dispersion contains 0.3 wt. % of pulp, then cationic starch (Neo-Posiparin made by Matsutani Chemical Industry Co.) of fixing agent is added to 0.5 wt. % of pulp, paper corresponding 80 g/m² is prepared in accordance with an ordinary process, dried in a rotary dryer of 110° C. for 120 sec. to prepare paper.

The obtained paper is measured for sizing degree after moistening in accordance with JIS, and listed in Table 2.

Table 2 shows the compositions which are allowed to stand for ten days, and the results of similar test to the previous examples are listed together with emulsion mean particle size (micron) of aqueous dispersions.

TABLE 2

| | Prepared composition | | Composition after 10 days | |
|---|---|---|---|---|
| Composition | Stockigt sizing (sec.) | Mean particle size (micron) of emulsion | Stockigt sizing (sec.) | Mean particle size (micron) of emulsion |
| (a) | 38 | <1 | 36 | <1 |
| (b) | 20 | approx. 1 | 18 | approx. 1 |
| (c) | 46 | <1 | 40 | <1 |
| (d) | 23 | approx. 1 | 19 | approx. 1 |
| (1) | 30 | approx. 1 | 5 | 5-6 |
| (2) | 11 | approx. 1 | 0 | 5-6 |

EXAMPLE 2

Comparison Example 2

Substituted alkenyl succinic anhydride and surfactant listed in predetermined columns of Table 3 are utilized, both are agitated and mixed under slow heating condition at an ambient temperature of 40° C. or lower, and compositions (e), (f), (g), (h) for sizing agent of the present invention and compositions (3), (4) for comparison are prepared.

The substituted alkenyl succinic anhydride A is maleic anhydride reacted with inner olefin having 15-18 carbon atoms, and the substituted alkenyl succinic anhydride B is maleic anhydride reacted with an oligomer mainly containing a pentamer of propylene.

TABLE 3

| Composition | Substituted alkenyl succinic anhydride | Surfactant |
|---|---|---|
| (e) | A 95 wt. % | Phosphates of polyoxyethylene nonyl phenol ether ester (mono-, di-mixture) (polyoxyethylene: n = 9) 5 wt. % |
| (f) | B 96 wt. % | Phosphates of polyoxyethylene nonyl phenol ether ester (mono-, di-mixture) (polyoxyethylene: n = 9) 4 wt. % |
| (g) | A 95 wt. % | Phosphates of polyoxyethylene tridecyl ether ester (mono-, di-mixture) (polyoxyethylene: n = 9) 5 wt. % |
| (h) | A 97 wt. % | Phosphates of polyoxyethylene nonyl phenol ether ester (mono-, di-mixture) (polyoxyethylene: n = 21.5) 3 wt. % |
| (3) | A 95 wt. % | Polyethylene nonyl phenol ether (polyoxyethylene: n = 15) 5 wt. % |
| (4) | A 96 wt. % | Sulfates of polyoxyethylene olenyl ether ester ammonium (polyoxyethylene: n = 18) 4 wt. % |

EXAMPLE 3

Comparison Example 3

Compositions (e) to (h) and (3), (4) prepared in the example 2 and comparison example 2 are filled in 5 wt. % of aqueous solution of aqueous soluble polymer compound listed in predetermined columns of Table 4, agitated at 50 V for 2 min. in a homomixer (HV-M type made by Tokushu Kika Kogyo Co.), thereby preparing aqueous dispersions.

The prepared aqueous dispersions are added to 2 wt. % pulp slurry containing 20 wt. % of pulp (L-BKP, c.s.F. 400 cc) of heavy calcium carbonate filler (Escalon #800 made by Sankyo Powder Co.) so that the composition of substituted alkenyl succinic anhydride and surfactant in the emulsion contains 0.5 wt. % of pulp, then cationic starch (Neo-Posiparin made by Matsutani Chemical Industry Co.) of fixing agent is added to 0.5 wt. % of pulp, paper corresponding 80 g/m² is prepared in accordance with a known process, dried in a rotary dryer of 110° C. for 120 sec. to prepare paper.

The obtained paper is measured for sizing degree after moistening in accordance with JIS, and listed in Table 4.

Table 4 shows the compositions which are allowed to stand for ten days, and the results of similar test to the previous examples are listed together with emulsion mean particle size (micron) of aqueous dispersions.

TABLE 4

| Composition | Aqueous polymer | | Part of solution to part of composition (part) | Prepared composition | | Composition after 10 days | |
|---|---|---|---|---|---|---|---|
| | | | | Stockigt sizing (sec.) | Mean particle site of emulsion (micron) | Stockigt sizing (sec.) | Mean particle site of emulsion (micron) |
| (1) | (e) | Cationic Starch | 40 | 37 | 1 | 31 | 1 |
| (2) | (e) | 90 mol % of acrylamide, 10 mol % of dimethylamino-ethylmethacrylate copolymer | 10 | 24 | 1 | 22 | 1 |
| (3) | (f) | Cationic Starch | 40 | 20 | approx. 1 | 19 | approx. 1 |
| (4) | (g) | Cationic Starch | 40 | 33 | 1 | 30 | 1 |
| (5) | (h) | 95 mol % of acrylamide, 5 mol % of dimethylamino-ethylmethacrylate benzyl chloride | 10 | 28 | approx. 1 | 27 | approx. 1 |
| (6) | (3) | Cationic Starch | 40 | 30 | 1 | 19 | 3–4 |
| (7) | (4) | Cationic Starch | 40 | 32 | approx. 1 | 17 | 4–5 |

What is claimed:

1. A composition for a sizing agent comprising (a) 70–99.9% by weight of a member selected from the group consisting of (1) substituted alkyl succinic anhydrides, the substituted alkyl succinic anhydride being an additive reaction product of a straight chain inner olefin having 12 to 36 carbon atoms and maleic anhydride, (2) substituted alkenyl succinic anhydrides and (3) mixtures thereof, and (b) 0.1–30% by weight of a member selected from the group consisting of phosphates of polyoxyethylene alkyl ether esters, phosphates of polyoxyethylene alkyl aryl ether esters and mixtures thereof.

2. The composition according to claim 1, wherein the phosphate of polyoxyethylene ether ester is a compound represented by the formula:

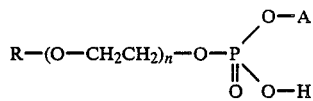

where R is an alkyl or alkyl aryl group having 8 or more carbon atoms; A represents H or $R'—(O—CH_2CH_2)_m$; n is an integer greater than or equal to 1; $R'$ is an alkyl or alkyl aryl group; and m is an integer greater than or equal to 1.

3. The composition according to claim 2, wherein:

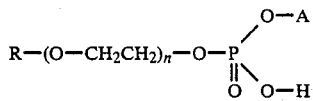

R is an alkyl or alkyl aryl group having 10–20 carbon atoms and n is an integer of 5 or more.

* * * * *